United States Patent
Wu et al.

(10) Patent No.: US 11,596,795 B2
(45) Date of Patent: Mar. 7, 2023

(54) THERAPEUTIC ELECTRICAL STIMULATION THERAPY FOR PATIENT GAIT FREEZE

(71) Applicant: Medtronic, Inc., Minneapolis, MN (US)

(72) Inventors: Jianping Wu, Shoreview, MN (US); Scott R. Stanslaski, Shoreview, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 1084 days.

(21) Appl. No.: 15/664,798

(22) Filed: Jul. 31, 2017

(65) Prior Publication Data
US 2019/0030338 A1    Jan. 31, 2019

(51) Int. Cl.
*A61N 1/36*    (2006.01)
*A61N 1/05*    (2006.01)
(Continued)

(52) U.S. Cl.
CPC ....... *A61N 1/36067* (2013.01); *A61N 1/0534* (2013.01); *A61N 1/36139* (2013.01);
(Continued)

(58) Field of Classification Search
CPC .............. A61N 1/36067; A61N 1/0534; A61N 1/36003; A61N 1/36139; A61N 1/36171;
(Continued)

(56) References Cited

U.S. PATENT DOCUMENTS

| 4,297,685 A | 10/1981 | Brainard, II |
| 4,550,736 A | 11/1985 | Broughton et al. |

(Continued)

FOREIGN PATENT DOCUMENTS

| DE | 19831109 A1 | 1/2000 |
| DE | 10024103 A1 | 11/2001 |

(Continued)

OTHER PUBLICATIONS

"Analysis of heart rate dynamics by methods derived from nonlinear mathematics: Clinical applicability and prognostic significance," http://herkules.oulu.fi.isbn9514250133/html, Oct. 2004, 4 pp.

(Continued)

*Primary Examiner* — Tammie K Marlen
(74) *Attorney, Agent, or Firm* — Shumaker & Sieffert, P.A.

(57) ABSTRACT

An implantable medical device (IMD) is described capable of determining whether a patient is susceptible to freezing of gait events during ambulatory movement without the patient demonstrating an episode of freezing of gait. In one example, the IMD senses, via one or more electrodes, a bioelectrical signal of a brain of the patient while the patient performs movement associated with freezing of gait. The IMD determines, based on the bioelectrical signal, whether the patient is susceptible to freezing of gait while the patient (Continued)

is not experiencing an episode of freezing of gait. Further, upon detecting the movement associated with freezing of gait, the IMD delivers electrical stimulation therapy to the patient configured to suppress freezing of gait.

26 Claims, 5 Drawing Sheets

(51) Int. Cl.
*A61N 1/372* (2006.01)
*A61N 1/02* (2006.01)

(52) U.S. Cl.
CPC ..... *A61N 1/36171* (2013.01); *A61N 1/37247* (2013.01); *A61N 1/025* (2013.01); *A61N 1/0531* (2013.01); *A61N 1/36135* (2013.01)

(58) Field of Classification Search
CPC .. A61N 1/37247; A61N 1/025; A61N 1/0531; A61N 1/36135; A61B 5/4064
See application file for complete search history.

(56) References Cited

U.S. PATENT DOCUMENTS

| | | |
|---|---|---|
| 4,771,780 A | 9/1988 | Sholder |
| 4,776,345 A | 10/1988 | Cohen et al. |
| 4,846,195 A | 7/1989 | Alt |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,233,984 A | 8/1993 | Thompson |
| 5,275,159 A | 1/1994 | Griebel |
| 5,335,657 A | 8/1994 | Terry, Jr. et al. |
| 5,337,758 A | 8/1994 | Moore et al. |
| 5,342,409 A | 8/1994 | Mullett |
| 5,469,861 A | 11/1995 | Piscopo et al. |
| 5,476,483 A | 12/1995 | Bornzin et al. |
| 5,509,927 A | 4/1996 | Epstein et al. |
| 5,514,162 A | 5/1996 | Bornzin et al. |
| 5,591,216 A | 1/1997 | Testerman et al. |
| 5,593,431 A | 1/1997 | Sheldon |
| 5,622,428 A | 4/1997 | Bonnet |
| 5,645,053 A | 7/1997 | Remmers et al. |
| 5,683,432 A | 11/1997 | Goedeke et al. |
| 5,713,923 A | 2/1998 | Ward et al. |
| 5,732,696 A | 3/1998 | Rapoport et al. |
| 5,782,884 A | 7/1998 | Stotts et al. |
| 5,814,093 A | 9/1998 | Stein |
| 5,833,709 A | 11/1998 | Rise et al. |
| 5,851,193 A | 12/1998 | Arikka et al. |
| 5,895,371 A | 4/1999 | Levitas et al. |
| 5,904,708 A | 5/1999 | Goedeke |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,999,846 A | 12/1999 | Pardey et al. |
| 6,044,297 A | 3/2000 | Sheldon et al. |
| 6,045,513 A | 4/2000 | Stone et al. |
| 6,059,576 A | 5/2000 | Brann |
| 6,091,973 A | 7/2000 | Colla et al. |
| 6,094,598 A | 7/2000 | Elsberry et al. |
| 6,095,991 A | 8/2000 | Krausman et al. |
| 6,102,874 A | 8/2000 | Stone et al. |
| 6,120,467 A | 9/2000 | Schallhorn |
| 6,128,534 A | 10/2000 | Park et al. |
| 6,157,857 A | 12/2000 | Dimpfel |
| 6,161,095 A | 12/2000 | Brown |
| 6,165,143 A | 12/2000 | Van Lummel |
| 6,227,203 B1 | 5/2001 | Rise et al. |
| 6,259,948 B1 | 7/2001 | Florio et al. |
| 6,273,856 B1 | 8/2001 | Sun et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,315,740 B1 | 11/2001 | Singh |
| 6,351,672 B1 | 2/2002 | Park et al. |
| 6,366,813 B1 | 4/2002 | DiLorenzo |
| 6,416,471 B1 | 7/2002 | Kumar et al. |
| 6,433,690 B2 | 8/2002 | Petelenz et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,234 B1 | 10/2002 | Van der Loos et al. |
| 6,466,821 B1 | 10/2002 | Pianca et al. |
| 6,468,234 B1 | 10/2002 | Van der Loos et al. |
| 6,514,218 B2 | 2/2003 | Yamamoto |
| 6,539,249 B1 | 6/2003 | Bonnet |
| 6,574,507 B1 | 6/2003 | Bonnet |
| 6,597,954 B1 | 7/2003 | Pless et al. |
| 6,605,038 B1 | 8/2003 | Teller et al. |
| 6,611,783 B2 | 8/2003 | Kelly, Jr. et al. |
| 6,626,902 B1 | 9/2003 | Kucharczyk et al. |
| 6,659,968 B1 | 12/2003 | McClure |
| 6,665,558 B2 | 12/2003 | Kalgren et al. |
| 6,687,538 B1 | 2/2004 | Hrdlicka et al. |
| 6,731,984 B2 | 5/2004 | Cho et al. |
| 6,735,474 B1 | 5/2004 | Loeb et al. |
| 6,752,766 B2 | 6/2004 | Kowallik et al. |
| 6,773,404 B2 | 8/2004 | Poezevera et al. |
| 6,819,956 B2 | 11/2004 | DiLorenzo |
| 6,878,121 B2 | 4/2005 | Krausman et al. |
| 6,881,192 B1 | 4/2005 | Park |
| 6,884,596 B2 | 4/2005 | Civelli et al. |
| 6,890,306 B2 | 5/2005 | Poezevera |
| 6,928,324 B2 | 8/2005 | Park et al. |
| 6,937,891 B2 | 8/2005 | Leinders et al. |
| 6,964,641 B2 | 11/2005 | Cho et al. |
| 6,993,380 B1 | 1/2006 | Modarres |
| 7,130,689 B1 | 10/2006 | Turcott |
| 7,141,034 B2 | 11/2006 | Eppstein et al. |
| 7,151,961 B1 | 12/2006 | Whitehurst et al. |
| 7,155,279 B2 | 12/2006 | Whitehurst et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,209,787 B2 | 4/2007 | DiLorenzo |
| 7,309,314 B2 | 12/2007 | Grant et al. |
| 7,313,440 B2 | 12/2007 | Miesel |
| 7,330,760 B2 | 2/2008 | Heruth et al. |
| 7,366,572 B2 | 4/2008 | Heruth et al. |
| 7,395,113 B2 | 7/2008 | Heruth et al. |
| 7,415,308 B2 | 8/2008 | Gerber et al. |
| 7,447,545 B2 | 11/2008 | Heruth et al. |
| 7,468,040 B2 | 12/2008 | Hartley et al. |
| 7,491,181 B2 | 2/2009 | Heruth et al. |
| 7,542,803 B2 | 6/2009 | Heruth et al. |
| 7,580,752 B2 | 8/2009 | Gerber et al. |
| 7,590,453 B2 | 9/2009 | Heruth et al. |
| 7,590,455 B2 | 9/2009 | Heruth et al. |
| 7,717,848 B2 | 5/2010 | Heruth et al. |
| 7,787,946 B2 | 8/2010 | Stahmann et al. |
| 7,792,583 B2 | 9/2010 | Miesel et al. |
| 7,805,196 B2 | 9/2010 | Miesel et al. |
| 7,853,322 B2 | 12/2010 | Bourget et al. |
| 7,881,798 B2 | 2/2011 | Heruth et al. |
| 7,908,013 B2 | 3/2011 | Miesel et al. |
| 8,032,224 B2 | 10/2011 | Miesel et al. |
| 8,190,253 B2 | 5/2012 | Heruth et al. |
| 8,244,340 B2 | 8/2012 | Wu et al. |
| 8,308,661 B2 | 11/2012 | Miesel et al. |
| 8,335,568 B2 | 12/2012 | Heruth et al. |
| 8,337,431 B2 | 12/2012 | Heruth et al. |
| 8,725,244 B2 | 5/2014 | Miesel et al. |
| 8,744,587 B2 | 6/2014 | Miesel et al. |
| 8,758,242 B2 | 6/2014 | Miesel et al. |
| 9,205,264 B2 | 12/2015 | Heruth et al. |
| 9,592,379 B2 | 3/2017 | Heruth et al. |
| 2001/0031930 A1 | 10/2001 | Roizen et al. |
| 2001/0037067 A1 | 11/2001 | Tchou et al. |
| 2001/0041831 A1 | 11/2001 | Starkweather et al. |

(56) References Cited

U.S. PATENT DOCUMENTS

| | | |
|---|---|---|
| 2001/0049471 A1 | 12/2001 | Suzuki et al. |
| 2002/0077562 A1 | 6/2002 | Kalgren et al. |
| 2002/0091308 A1 | 7/2002 | Kipshidze et al. |
| 2002/0161412 A1 | 10/2002 | Sun et al. |
| 2002/0169485 A1 | 11/2002 | Pless et al. |
| 2002/0177882 A1 | 11/2002 | DiLorenzo |
| 2002/0193697 A1 | 12/2002 | Cho et al. |
| 2002/0193839 A1 | 12/2002 | Cho et al. |
| 2003/0004423 A1 | 1/2003 | Lavie et al. |
| 2003/0135917 A1 | 7/2003 | Ruane |
| 2003/0139692 A1 | 7/2003 | Barrey et al. |
| 2003/0149457 A1 | 8/2003 | Tcheng et al. |
| 2003/0153953 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171791 A1 | 9/2003 | KenKnight et al. |
| 2003/0195588 A1 | 10/2003 | Fischell et al. |
| 2003/0204219 A1 | 10/2003 | Gielen |
| 2003/0212445 A1 | 11/2003 | Weinberg |
| 2004/0002741 A1 | 1/2004 | Weinberg |
| 2004/0002742 A1 | 1/2004 | Florio |
| 2004/0015103 A1 | 1/2004 | Aminian et al. |
| 2004/0049132 A1 | 3/2004 | Barron et al. |
| 2004/0077995 A1 | 4/2004 | Ferek-Petric et al. |
| 2004/0088025 A1 | 5/2004 | Gesotti |
| 2004/0102814 A1 | 5/2004 | Sorenson et al. |
| 2004/0111040 A1 | 6/2004 | Ni et al. |
| 2004/0111041 A1 | 6/2004 | Ni et al. |
| 2004/0138719 A1 | 7/2004 | Cho et al. |
| 2004/0199217 A1 | 10/2004 | Lee et al. |
| 2004/0215269 A1 | 10/2004 | Burnes et al. |
| 2004/0220621 A1 | 11/2004 | Zhou et al. |
| 2005/0021103 A1 | 1/2005 | DiLorenzo |
| 2005/0021104 A1 | 1/2005 | DiLorenzo |
| 2005/0039745 A1 | 2/2005 | Stahmann et al. |
| 2005/0042589 A1 | 2/2005 | Hatlestad et al. |
| 2005/0060001 A1 | 3/2005 | Singhal et al. |
| 2005/0061320 A1 | 3/2005 | Lee et al. |
| 2005/0065560 A1 | 3/2005 | Lee et al. |
| 2005/0076908 A1 | 4/2005 | Lee et al. |
| 2005/0080463 A1 | 4/2005 | Stahmann et al. |
| 2005/0081847 A1 | 4/2005 | Lee et al. |
| 2005/0085738 A1 | 4/2005 | Stahmann et al. |
| 2005/0113710 A1 | 5/2005 | Stahmann et al. |
| 2005/0115561 A1 | 6/2005 | Stahmann et al. |
| 2005/0119703 A1 | 6/2005 | DiLorenzo |
| 2005/0143617 A1 | 6/2005 | Auphan |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222626 A1 | 10/2005 | DiLorenzo |
| 2005/0222643 A1 | 10/2005 | Heruth et al. |
| 2005/0234514 A1 | 10/2005 | Heruth et al. |
| 2005/0234518 A1 | 10/2005 | Heruth et al. |
| 2005/0240086 A1 | 10/2005 | Akay |
| 2005/0240242 A1 | 10/2005 | DiLorenzo |
| 2005/0245790 A1 | 11/2005 | Bergfalk et al. |
| 2005/0245988 A1 | 11/2005 | Miesel |
| 2006/0224191 A1 | 10/2006 | DiLorenzo |
| 2006/0235472 A1 | 10/2006 | Goetz et al. |
| 2006/0293720 A1 | 12/2006 | DiLorenzo |
| 2007/0038265 A1 | 2/2007 | Tcheng et al. |
| 2007/0046408 A1 | 3/2007 | Shim |
| 2007/0073355 A1 | 3/2007 | DiLorenzo |
| 2007/0142862 A1 | 6/2007 | DiLorenzo |
| 2007/0250134 A1* | 10/2007 | Miesel ............... A61B 5/0488 607/45 |
| 2007/0255118 A1 | 11/2007 | Miesel et al. |
| 2007/0276439 A1 | 11/2007 | Miesel et al. |
| 2008/0154111 A1 | 6/2008 | Wu et al. |
| 2009/0030263 A1 | 1/2009 | Heruth et al. |
| 2009/0036951 A1 | 2/2009 | Heruth et al. |
| 2009/0082691 A1 | 3/2009 | Denison et al. |
| 2009/0099627 A1 | 4/2009 | Molnar et al. |
| 2013/0150921 A1 | 2/2013 | Singhal et al. |
| 2013/0331906 A1 | 12/2013 | Krueger et al. |
| 2014/0222101 A1 | 8/2014 | Miesel et al. |
| 2016/0158552 A1 | 6/2016 | Heruth et al. |
| 2016/0263382 A1 | 9/2016 | Heruth et al. |
| 2017/0156663 A1 | 6/2017 | Heruth et al. |
| 2017/0165481 A1 | 6/2017 | Menon |

FOREIGN PATENT DOCUMENTS

| | | |
|---|---|---|
| EP | 0564803 A1 | 10/1993 |
| EP | 0849715 B1 | 6/1998 |
| EP | 1195139 A1 | 4/2002 |
| EP | 1308182 A2 | 5/2003 |
| EP | 1437159 A1 | 7/2004 |
| EP | 1322227 B1 | 12/2005 |
| GB | 2330912 A | 5/1999 |
| WO | 1998/000197 A1 | 1/1998 |
| WO | 1999/013765 A1 | 3/1999 |
| WO | 2001/037930 A1 | 5/2001 |
| WO | 2002/028282 A1 | 4/2002 |
| WO | 2002/041771 A1 | 5/2002 |
| WO | 2002/087433 A1 | 11/2002 |
| WO | 2002/096512 A1 | 12/2002 |
| WO | 2002/100267 A1 | 12/2002 |
| WO | 2003/024325 A2 | 3/2003 |
| WO | 1291036 A2 | 3/2003 |
| WO | 2003/051356 A1 | 6/2003 |
| WO | 2003/065891 A1 | 8/2003 |
| WO | 2005/028029 A2 | 3/2005 |
| WO | WO 2005/020866 | 3/2005 |
| WO | 2005/035050 A1 | 4/2005 |

OTHER PUBLICATIONS

"Bilateral Comparisons of the BiteStrip Bruxism Device and Masseter EMG Bruxism Events," downloaded from Internet Archive of ww.quietsleep.com dated Jan. 29, 2005, http://web.archive.org/web/20041124075114/www.quietsleep.com/pdf/Bilateral+Comparisons.pdf, 1 pp.

"Bitestrip Flier," downloaded from Internet Archive of www.quietsleep.com dated Jan. 29, 2005, http://webarchive.org/web/20041124080003/www.quietsleep.com/pdf/bitestrip+Flier.pdf., 1 pp.

Van Dam et al., "Measuring physical activity in patients after surgery for a malignant tumour in the leg," The Journal of Bone & Joint Surgery, vol. 83-B, No. 7, Sep. 2001, pp. 1015-1019.

"Design Competition: Runners-Up for the Best Three Designs," EPN, vol. 26, No. 1, Jan. 2002, 1 pp.

"IBM & Citizen Watch develop Linux-based 'WatchPad'," http://www.linuxdevices.com/news/NS6580187845.html, Retrieved on Feb. 20, 2006, 5 pp.

"MiniMitter® Physiological and Behavioral Monitoring for Humans and Animals," http://www.minimitter.com/Products/Actiwatch, Retrieved on Feb. 20, 2006, 3 pp.

"The BiteStrip: A Novel Screener for Sleep Bruxism," downloaded from Internet Archive of www.quietsleep.com dated Jan. 29, 2005, http://http.web.archive.org/web/20041124072922/www.quietsleep.com/pdf/BiteStrip-+Novel+Screener.pdf., 1 pp.

"Watch," Wikipedia, the free encyclopedia, http://en.wikipedia.org/wiki/Watch, Feb. 20, 2006, 6 pp.

Aminian et al., "Physical Activity Monitoring Based on Accelerometry: Validation and Comparison with Video Observation," Medical & Biological Engineering & Computing, vol. 37, No. 2, Mar. 1999, pp. 304-308.

Amzica, "Physiology of Sleep and Wakefulness as it Relates to the Physiology of Epilepsy," Journal of Clinical Neurophysiology, American Clinical Neurophysiology Society, 19(6), Dec. 2002, pp. 488-503.

(56) References Cited

OTHER PUBLICATIONS

Antonini et al., "Deep brain stimulation and its effect on sleep in Parkinson's disease," Sleep Medicine, vol. 5, Issue 2, Mar. 2004, pp. 211-214.
Cicolin et al., "Effects of deep brain stimulation of the subthalamic nucleus on sleep architecture in parkinsonian patients," Sleep Medicine, vol. 5, Issue 2, Mar. 2004, pp. 207-210.
Criticare System Inc., -504DX Portable Pulse Oximeter, http;//www.csiusa.com/504dx.html, Jan. 31, 2005, 4 pp.
Dinner, "Effect of Sleep of Epilepsy," Journal of Clinical Neurophysiology, American Clinical Neurophysiology Society, 19(6), Dec. 2002, pp. 504-513.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Societ, 19(6), Dec. 2002, pp. 514-521.
Goodrich et al., "The Prediction of Pain Using Measures of Sleep Quality," Pain Digest, 8, 1998, pp. 23-25 (Applicant points out that, in accordance with MPEP 609.04(a), the 1998 year of publication is sufficiently earlier than the effective U.S. filing date and any foreign priority date so that the particular month of publication is not in issue.).
Greenberg, MD, Phd. et al., "Mechanisms and the current state of deep brain stimulation in neuropsychiatry," CNS Spectrums, vol. 8, No. 7, Jul. 2003, pp. 522-526.
Itamar Medical Information, http://itamar-medical.com/content.asp?id=31, Jan. 31, 2005, 2 pp.
Kassam, "2005 EDP Topic 'MK4': Tremor Data-Logger for Parkinson's Disease Patients," http://www.ee.ryerson.ca/~courses/edp2005/MK4.html, Feb. 20, 2006, 3 pp.
Kerr et al., "Analysis of the sit-stand-sit movement cycle in normal subjects," Clinical Bimechanics, vol. 12, No. 4, Jun. 1997, pp. 236-245.
MAP Medizin—Technologic GmbH, Poly-MESAM®, http://195.244.124.130/map/de/eng/map_med.nsf/cmsall/705643A3FCBE4188AC1256EF4 . . . , Jan. 31, 2005, 4 pp.
Medcare—A Global Leader in Sleep Diagnostics, Embletta Recording System, http://www.medcare.com/products/diagnostic/embletta/, Jan. 31, 2005, 2 pp.
Medcare—A Global Leader in Sleep Diagnostics, Somnologica for Embeltta, http://www.medcare.com/products/diagnostic/embletta/SomnoEmbletta/index.asp, Jan. 31, 2005, 1 pp.
Mendez et al., "Interactions Between Sleep and Epilepsy," Journal of Clinical Neurophysiology American Clinical Neurophysiology Society, 18(2), Mar. 2001, pp. 106-127.
Merlin, http://www.aha.ru/~pir/english/merlin, Jan. 31, 2005, 4 pp.
Oerlemans et al., "The prevalence of sleep disorders in patients with Parkinson's disease. A self-reported, community-based survey," Sleep Medicine, vol. 3, Issue 2, Mar. 2002, pp. 147-149.
Sleep Solutions—PR Newsire: Sleep Solutions Introduces NovaSom™ OSG™ for PSG . . . , http://www.sleep-solutions.com/press_room/novasom.htm, Jan. 31, 2005, 2 pp.
Sleep Strip & Bite Strip, http://www.quietsleep.com/snoringapnea/sleepstrip.htm, Jan. 31, 2005, 7 pp.
Smith, et al., "How do sleep disturbance and chronic pain interrelate? Insights form the longitudinal and cognitive-behavioral clinical trials literature," Sleep Medicine Reviews, YSMRV 286, Jun. 19, 2003, 14 pp.
Smith, et al., "Presleep Cognitions in Patients with Insomnia Secondary to Chronic Pain," Journal of Behavioral Medicine, vol. 24, No. 1, Feb. 2001, pp. 93-114.
Snap® Laboratories, Product Fact Sheet, http://www.snaplab.com/mp_fact.htm, Jan. 31, 2005, 2 pp.
Tuisku, "Motor Activity Measured by Actometry in Neuropsychiatric Disorders," Department of Psychiatry, University of Helsinki, Helsinki, Finland, Dec. 13, 2002, 115 pp.
Singh et al., "Freezing of Gait-Related Oscillatory Activity in the Human Subthalamic Nucleus." Basal Ganglia, vol. 3, No. 1, Mar. 1, 2013, pp. 25-32.
Ricchi et al., "Transient Effects of 80 Hz Stimulation on Gait in STN-DBS Treated PD Patients: A 15 Months Follow-Up Study," Brain Stimulation, vol. 5, No. 3. Jul. 1, 2012, pp. 388-392.
Toledo et al., "High-Beta Activity in the Subthalmic Nucleus and Freezing of Gait in Parkinson's Disease," Neurobiology of Disease, vol. 64, Jan. 1, 2014, pp. 60-65.
International Search Report and Written Opinion of International Application No. PCT/US2018/027144, dated Jun. 15, 2018, 14 pp.
Examination Report from counterpart European Application No. 18721592.6, dated Apr. 8, 2021, 6 pp.
Office Action, and translation thereof, from counterpart Japanese Application No. 2020-505161 dated Dec. 3, 2021, 8 pp.
Communication pursuant to Article 94(3) EPC from counterpart European Application No. 18721592.6 dated Dec. 23, 2021, 6 pp.
Office Action, and translation thereof, from counterpart Japanese Application No. 2020-505161, dated Feb. 21, 2022, 9 pp.
Response to Examination Report dated Dec. 23, 2021 from counterpart European Application No. 18721592.6, filed May 2, 2022, 10pp.

* cited by examiner

THERAPEUTIC ELECTRICAL STIMULATION THERAPY FOR PATIENT GAIT FREEZE

TECHNICAL FIELD

This disclosure generally relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Patients afflicted with movement disorders or other neurodegenerative impairment, whether by disease or trauma, may experience muscle control and movement problems, such as rigidity, bradykinesia (i.e., slow physical movement), rhythmic hyperkinesia (e.g., tremor), nonrhythmic hyperkinesia (e.g., tics) or akinesia (i.e., a loss of physical movement). Movement disorders may be found in patients with Parkinson's disease, multiple sclerosis, and cerebral palsy, among other conditions. Delivery of electrical stimulation and/or a fluid (e.g., a pharmaceutical drug) by a medical device to one or more sites in a patient, such as a brain, spinal cord, leg muscle or arm muscle, in a patient may help alleviate, and in some cases, eliminate symptoms associated with movement disorders.

SUMMARY

In some examples, the disclosure describes techniques for determining whether a patient is susceptible to episodes of freezing of gait during ambulatory movement without the patient demonstrating episodes of freezing of gait. For example, an implantable medical device (IMD) may sense a bioelectrical signal of a brain of the patient while the patient performs a movement associated with freezing of gait, and then determine, based on the bioelectrical signal, that the patient is susceptible to episodes of freezing of gait even though the patient may not actively be experiencing episodes of freezing of gait.

In another example of the techniques of the disclosure, an IMD is implanted within a patient suffering from freezing of gait. The IMD stores a first set of therapy parameters for the delivery of electrical stimulation therapy configured to suppress freezing of gait. The IMD further stores a second set of therapy parameters for the delivery of electrical stimulation therapy configured to suppress symptoms of Parkinson's disease other than freezing of gait. Upon detecting that a patient is performing the movement associated with freezing of gait, the IMD may activate or switch from delivery of the electrical stimulation therapy configured to suppress symptoms of Parkinson's disease other than freezing of gait to delivery of the electrical stimulation therapy configured to suppress freezing of gait.

In one example, this disclosure describes a method including: sensing, by one or more processors and via one or more electrodes, a bioelectrical signal of a brain of a patient while the patient performs movement associated with freezing of gait; determining, by the one or more processors and based on the bioelectrical signal, that the patient is susceptible to freezing of gait while the patient is not experiencing an episode of freezing of gait; and programming, by the one or more processors and based on the determination, a medical device to deliver electrical stimulation therapy to the patient configured to suppress freezing of gait upon detecting movement associated with freezing of gait.

In another example, this disclosure describes a medical system including: one or more electrodes configured to sense a bioelectrical signal of a brain of a patient while the patient performs movement associated with freezing of gait; and one or more processors configured to: determine, based on the bioelectrical signal, that the patient is susceptible to freezing of gait while the patient is not experiencing an episode of freezing of gait; and program, based on the determination, a medical device to deliver, to the patient, electrical stimulation therapy configured to suppress freezing of gait upon detecting movement associated with freezing of gait.

In another example, this disclosure describes a non-transitory computer-readable medium including instructions, that, when executed, cause one or more processors to: sense, via one or more electrodes, a bioelectrical signal of a brain of a patient while the patient performs movement associated with freezing of gait; determine, based on the bioelectrical signal, that the patient is susceptible to freezing of gait while the patient is not experiencing an episode of freezing of gait; and program, based on the determination, a medical device to deliver electrical stimulation therapy to the patient configured to suppress freezing of gait upon detecting movement associated with freezing of gait.

In another example, this disclosure describes a medical system including: means for sensing a bioelectrical signal of a brain of a patient while the patient performs movement associated with freezing of gait; means for determining, based on the bioelectrical signal, that the patient is susceptible to freezing of gait while the patient is not experiencing an episode of freezing of gait; and means for programming, based on the determination, a medical device to deliver electrical stimulation therapy to the patient configured to suppress freezing of gait upon detecting movement associated with freezing of gait.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
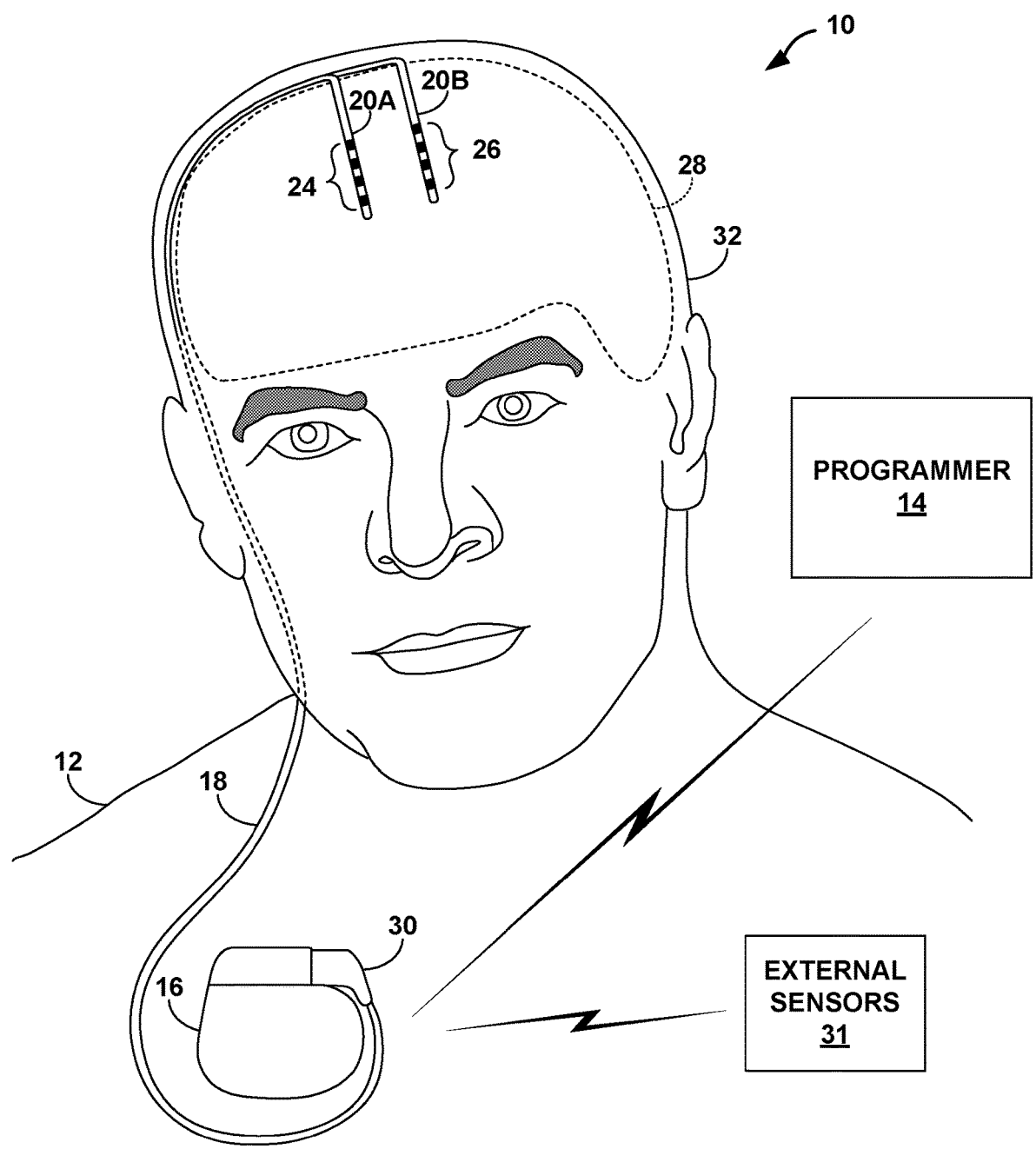
FIG. 1 is a conceptual diagram illustrating an example therapy delivery system for delivering electrical stimulation therapy in accordance with the techniques of the disclosure.

Systems, devices, and techniques are described for monitoring a bioelectrical signal of a brain of a patient to objectively determine whether the patient suffers from or is susceptible to suffering from freezing of gait. Patients suffering from Parkinson's disease may experience gait and balance problems, such as episodes of freezing of gait during movement. Freezing of gait is a condition wherein motor control of a patient is disrupted such that the patient's ability to move or walk is temporarily interrupted. A patient suffering from freezing of gait may experience episodes of freezing of gait that appear at unpredictable times and/or for unpredictable durations. However, not all patients suffering from Parkinson's disease experience freezing of gait. For example, some patients, without or in addition to experiencing freezing of gait, may experience other symptoms of Parkinson's disease, such as bradykinesia, rigidity, tremor, and/or other undesirable manifestations.

High frequency deep brain stimulation (DBS) (e.g., DBS having a frequency selected from a range of about 130 Hertz to about 185 Hertz) may effectively suppress symptoms of Parkinson's disease other than freezing of gait, such as bradykinesia, rigidity, or tremor, and/or other manifestations. However, high frequency DBS may not be effective for suppressing freezing of gait. Thus, a patient suffering from freezing of gait as well as other undesirable symptoms of Parkinson's disease may require differing DBS therapy at different times to effectively manage each of his or her symptoms. Furthermore, during a programming session where therapy parameters for DBS are configured, it may be difficult for a clinician to determine if a patient suffers from freezing of gait unless the clinician concurrently observes the patient experiencing an episode of freezing of gait.

In accordance with the techniques of the disclosure, systems, devices, and techniques are described for objectively determining whether the patient suffers from or is susceptible to suffering from freezing of gait, even when the patient is not experiencing an episode of freezing of gait, by sensing bioelectrical signals of a brain of the patient. In one example of the techniques of the disclosure, an IMD is configured to monitor a bioelectrical signal of a brain of a patient while the patient is not experiencing an episode of freezing of gait, and, based on the sensed bioelectrical signal, determine whether or not the patient suffers from or is susceptible to suffering from freezing of gait. For example, the bioelectrical signal of the brain of a patient suffering from freezing of gait may demonstrate changes in patterns when the patient transitions into movement associated with freezing of gait. Such a movement associated with freezing of gait may be a movement that is accompanied by freezing of gait in the patient or that is susceptible to disruption or interruption by an episode of freezing of gait. Some examples of movement associated with freezing of gait include stepping, turning, walking, transitioning from standing to stepping, or waving arms. Other examples of movement associated with freezing of gait include any movement or motion where the patient is upright and moving his or her legs. In contrast, the same bioelectrical signal of a brain of a patient not suffering from freezing of gait may not exhibit these changes in patterns during movement associated with freezing of gait.

As one example, the IMD may compare an amplitude of a Beta frequency band of local field potentials of the brain of the patient while the patient is not moving to an amplitude of the Beta frequency band while the patient performs a movement associated with freezing of gait, such as turning, stepping, or transitioning from standing to stepping. Upon detecting that the amplitude of the Beta frequency band while the patient performs the movement associated with freezing of gait substantially decreases in comparison to the amplitude of the Beta frequency band while the patient is not moving, the IMD determines that the patient is susceptible to episodes of freezing of gait. Therefore, by examining bioelectrical signals of the brain, a system implementing the techniques of the disclosure may allow for an objective determination of whether the patient suffers from or is susceptible to suffering from freezing of gait, even without the patient demonstrating an episode of freezing of gait.

Additionally, for a patient that is susceptible to freezing of gait, an IMD for the patient may deliver a first therapy configured to suppress symptoms of Parkinson's disease other than freezing of gait until a movement associated with freezing of gait is detected. In response to the detected movement associated with freezing of gait, the IMD may temporarily adjust the therapy to deliver a second therapy configured to suppress freezing of gait, until the movement associated with freezing of gait is no longer detected. In another example, an IMD may temporarily adjust one or more therapy parameters of electrical stimulation therapy delivered to a patient in response to detecting movement associated with freezing of gait.

As one example, an IMD implantable in a patient suffering from freezing of gait may store multiple DBS therapy settings. The IMD delivers DBS therapy at a first frequency to provide therapy for symptoms of Parkinson's disease other than freezing of gait, such as bradykinesia, rigidity, or tremor. Upon detecting a movement by the patient associated with freezing of gait, such as transitioning from standing to walking or turning, the IMD switches from delivering the DBS therapy at the first frequency to delivering the DBS therapy at a second frequency to suppress freezing of gait. Upon detecting that the patient has ceased the movement associated with freezing of gait, the IMD switches from delivering the DBS therapy at the second frequency to delivering the DBS therapy at the first frequency to resume providing therapy for the other undesirable symptoms. Accordingly, a system according to the techniques herein may provide therapy configured to suppress freezing of gait only when the patient requires such therapy, and otherwise provide therapy effective at suppressing other undesirable symptoms of Parkinson's disease when the patient does not require therapy for freezing of gait.

FIG. 1 is a conceptual diagram illustrating an example therapy system 10 in accordance with examples of the disclosure. In FIG. 1, example therapy system 10 may deliver electrical stimulation therapy to treat or otherwise manage a patient condition, such as, e.g., a movement disorder of patient 12. One example of a movement disorder treated by the delivery of DBS via system 10 may include Parkinson's disease. Patient 12 ordinarily will be a human patient. In some cases, however, therapy system 10 may be applied to other mammalian or non-mammalian non-human patients.

For ease of illustration, examples of the disclosure will primarily be described with regard to the treatment of movement disorders and, in particular, the treatment of Parkinson's disease, e.g., by reducing or preventing the manifestation of symptoms exhibited by patients suffering from Parkinson's disease. As noted above, such symptoms may include rigidity, akenesia, bradykinesia, diskensia, and/or resting tremor. However, the treatment of one or more patient disorders other than that of Parkinson's disease by employing the techniques described herein is contemplated. For example, the described techniques may be employed to manage or other treat symptoms of other patient disorders, such as, but not limited to, psychological disorders, mood disorders, seizure disorders or other neurogenerative impairment. In one example, such techniques may be employed to provide therapy to patient to manage Alzheimer's disease.

Therapy system 10 includes medical device programmer 14, implantable medical device (IMD) 16, lead extension 18, and one or more leads 20A and 20B (collectively "leads 20) with respective sets of electrodes 24, 26. IMD 16 includes a stimulation therapy module that includes a stimulation generator that generates and delivers electrical stimulation therapy to one or more regions of brain 28 of patient 12 via a subset of electrodes 24, 26 of leads 20A and 20B, respectively. In the example shown in FIG. 1, therapy system 10 may be referred to as a deep brain stimulation (DBS) system because IMD 16 provides electrical stimulation therapy directly to tissue within brain 28, e.g., a tissue site under the dura mater of brain 28. In other examples, leads 20 may be positioned to deliver therapy to a surface of brain 28 (e.g., the cortical surface of brain 28).

In some examples, delivery of stimulation to one or more regions of brain 28, such as an anterior nucleus (AN), thalamus or cortex of brain 28, provides an effective treatment to manage a disorder of patient 12. In some examples, IMD 16 may provide cortical stimulation therapy to patient 12, e.g., by delivering electrical stimulation therapy to one or more tissue sites in the cortex of brain 28. In cases in which IMD 16 delivers electrical stimulation therapy to brain 28 to treat Parkinson's disease, target stimulation sites may include one or more basal ganglia sites, including, e.g., subthalamic nucleus (STN), globus pallidus interna (GPi), globus pallidus externa (GPe), pedunculopontine nucleus (PPN), thalamus, substantia nigra pars reticulata (SNr), internal capsule, and/or motor cortex. In the example shown in FIG. 1, IMD 16 may be implanted within a subcutaneous pocket above the clavicle of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. Generally, IMD 16 is constructed of a biocompatible material that resists corrosion and degradation from bodily fluids. IMD 16 may comprise a hermetic housing 34 to substantially enclose components, such as a processor, therapy module, and memory.

Leads 20A and 20B may be implanted within the right and left hemispheres, respectively, of brain 28 in order deliver electrical stimulation therapy to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere or IMD 16 may be coupled to a single lead that is implanted in one or both hemispheres of brain 28.

Leads 20 may be positioned to deliver electrical stimulation therapy to one or more target tissue sites within brain 28 to manage patient symptoms associated with a disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation therapy to target tissue sites within brain 28 during treatment. For example, in the case of Parkinson's disease, for example, leads 20 may be implanted to deliver electrical stimulation therapy to one or more basal ganglia sites, including, e.g., subthalamic nucleus (STN), globus pallidus interna (GPi), globus pallidus externa (GPe), pedunculopontine nucleus (PPN), thalamus, substantia nigra pars reticulata (SNr), internal capsule, and/or motor cortex.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

Leads 20 may deliver electrical stimulation therapy to treat any number of neurological disorders or diseases in addition to movement disorders, such as seizure disorders or psychiatric disorders. Examples of movement disorders include a reduction in muscle control, motion impairment or other movement problems, such as rigidity, bradykinesia, rhythmic hyperkinesia, nonrhythmic hyperkinesia, dystonia, tremor, and akinesia. Movement disorders may be associated with patient disease states, such as Parkinson's disease or Huntington's disease. Examples of psychiatric disorders include MDD, bipolar disorder, anxiety disorders, post traumatic stress disorder, dysthymic disorder, and OCD. As described above, while examples of the disclosure are primarily described with regard to treating Parkinson's disease, treatment of other patient disorders via delivery of therapy to brain 28 is contemplated.

Leads 20 may be implanted within a desired location of brain 28 via any suitable technique, such as through respective burr holes in a skull of patient 12 or through a common burr hole in the cranium 32. Leads 20 may be placed at any location within brain 28 such that electrodes 24, 26 of leads 20 are capable of providing electrical stimulation therapy to targeted tissue during treatment. Electrical stimulation therapy generated from the stimulation generator (not shown) within the therapy module of IMD 16 may help prevent the onset of events associated with the patient's disorder or mitigate symptoms of the disorder.

In the examples shown in FIG. 1, electrodes 24, 26 of leads 20 are shown as ring electrodes. Ring electrodes may be relatively easy to program and are typically capable of delivering an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields. The complex electrode array geometry may include multiple electrodes (e.g., partial ring or segmented electrodes) around the perimeter of each lead 20, rather than a ring electrode. In this manner, electrical stimulation therapy may be directed to a specific direction from leads 20 to enhance therapy efficacy and reduce possible adverse side effects from stimulating a large volume of tissue.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In alternative examples, leads 20 may have shapes other than elongated cylinders as shown in FIG. 1. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs. A therapy program may define one or more electrical stimulation therapy parameter values for therapy generated and delivered from IMD 16 to brain 28 of patient 12. Where IMD 16 delivers electrical stimulation therapy in the form of electrical pulses, for example, the stimulation therapy may be characterized by selected pulse parameters, such as pulse amplitude, pulse rate or pulse frequency, and pulse width. Where IMD 16 delivers electrical stimulation therapy in the form of a sinusoidal wave, for example, the stimulation therapy may be characterized by selected parameters, such as a waveform amplitude and cycle frequency. In addition, if different electrodes are available for delivery of stimulation, the therapy may be further characterized by different electrode combinations, which can include selected electrodes and their respective polarities. The exact therapy parameter values of the stimulation therapy that helps manage or treat a patient disorder may be specific for the particular target stimulation site (e.g., the region of the brain) involved as well as the particular patient and patient condition.

In addition to delivering therapy to manage a disorder of patient 12, therapy system 10 monitors one or more bioelectrical brain signals of patient 12. For example, IMD 16 may include a sensing module that senses bioelectrical brain signals within one or more regions of brain 28. In the example shown in FIG. 1, the signals generated by electrodes 24, 26 are conducted to the sensing module within IMD 16 via conductors within the respective lead 20A, 20B. As described in further detail below, in some examples, a processor of IMD 16 may sense the bioelectrical signals within brain 28 of patient 12 and control delivery of electrical stimulation therapy to brain 28 via electrodes 24, 26. For example, IMD 16 may sense a Beta signal comprising a frequency within about 11 Hertz to about 30 Hertz of brain 28 of patient 12.

In some examples, the sensing module of IMD 16 may receive the bioelectrical signals from electrodes 24, 26 or other electrodes positioned to monitored brain signals of patient 12. Electrodes 24, 26 may also be used to deliver electrical stimulation therapy from the therapy module to target sites within brain 28 as well as sense brain signals within brain 28. However, IMD 16 can also use separate sensing electrodes to sense the bioelectrical brain signals. In some examples, the sensing module of IMD 16 may sense bioelectrical brain signals via one or more of the electrodes 24, 26 that are also used to deliver electrical stimulation therapy to brain 28. In other examples, one or more of electrodes 24, 26 may be used to sense bioelectrical brain signals while one or more different electrodes 24, 26 may be used to deliver electrical stimulation therapy.

Depending on the particular stimulation electrodes and sense electrodes used by IMD 16, IMD 16 may monitor brain signals and deliver electrical stimulation therapy at the same region of brain 28 or at different regions of brain 28. In some examples, the electrodes used to sense bioelectrical brain signals may be located on the same lead used to deliver electrical stimulation therapy, while in other examples, the electrodes used to sense bioelectrical brain signals may be located on a different lead than the electrodes used to deliver electrical stimulation therapy. In some examples, a brain signal of patient 12 may be monitored with external electrodes, e.g., scalp electrodes. Moreover, in some examples, the sensing module that senses bioelectrical brain signals of brain 28 (e.g., the sensing module that generates an electrical signal indicative of the activity within brain 28) is in a physically separate housing from outer housing 34 of IMD 16. However, in the example shown in FIG. 1 and the example primarily referred to herein for ease of description, the sensing module and therapy module of IMD 16 are enclosed within a common outer housing 34.

The bioelectrical brain signals monitored by IMD 16 may reflect changes in electrical current produced by the sum of electrical potential differences across brain tissue. Examples of the monitored bioelectrical brain signals include, but are not limited to, an electroencephalogram (EEG) signal, an electrocorticogram (ECoG) signal, a local field potential (LFP) sensed from within one or more regions of a patient's brain and/or action potentials from single cells within the patient's brain.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the position of leads 20 within brain 28, initial programs defining therapy parameter values, and any other information that may be useful for programming into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that may provide efficacious therapy to patient 12 to address symptoms associated with the seizure disorder (or other patient condition). For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more physiological parameters of patient (e.g., heart rate, respiratory rate or muscle activity). Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

In one example of the techniques of the disclosure, IMD 16 senses a bioelectrical signal of brain 28 of patient 12 via leads 20A and 20B. In one example, IMD 16 may directly record local field potentials of a subthalamic nucleus of brain 28 of patient 12 via leads 20A and 20B. Such local field potentials may be detected in the subthalamic nucleus (STN), globus pallidus interna (GPi), globus pallidus externa (GPe), and/or other areas of the basal ganglia. In this example, the local field potentials in brain 28 of a patient 12 suffering from or susceptible to suffering from freezing of gait exhibit changes in a Beta frequency (e.g., between about 11 Hz to about 30 Hz) when the patient transitions into a movement associated with freezing of gait. Further, local field potentials in brain 28 of a patient 12 not suffering from freezing of gait may not demonstrate such changes. In this fashion, the Beta frequency of the local field potentials in the brain of the patient may be said to be a biomarker for freezing of gait. In other worlds, the Beta frequency response of the local field potentials may serve as an indicator as to whether or not the patient suffers or is susceptible to suffering from of freezing of gait, even though the patient may not presently be experiencing an episode of freezing of gait.

While FIG. 1 depicts IMD 16 making use of sensors disposed along implanted leads 20A-20B, in other examples, IMD 16 records the local field potentials with external sensors 31. As described herein, the amplitude of local field potentials of a patient suffering from freezing of gait demonstrate changes in patterns when the patient transitions into movement. For example, the amplitude of local field potentials within a Beta band (e.g., about 13 Hertz to about 30 Hertz) of the patient suffering from freezing of gait decreases significantly when the patient transitions from standing to stepping even when the patient is not experiencing episodes of freezing of gait. In contrast, the amplitude of local field potentials of a patient not suffering from freezing of gait do not exhibit these changes in patterns. For example, the amplitude of local field potentials within the Beta band of a brain of the patient not suffering from freezing of gait does not significantly change when the patient transitions activity from standing to stepping. By comparing the amplitude of local field potentials in a subthalamic nucleus of a patient, the techniques of the disclosure may allow for an objective determination of whether the patient suffers from or is susceptible to suffering from freezing of gait without the patient actively demonstrating episodes of freezing of gait.

As an example of the above, one or more processors monitor, via one or more electrodes 24, 26 disposed along leads 20A-20B, a bioelectrical signal, such as a Beta signal, of brain 28 of patient 12. In some examples, the one or more processors are located within IMD 16, while in other examples, the one or more processors are located within external programmer 14. The one or more processors sense, via the one or more electrodes 24, 26, a first amplitude of the bioelectrical signal while patient 12 is not moving. Further, the one or more processors sense, via the one or more electrodes 24, 26, a second amplitude of the bioelectrical signal while patient 12 is performing a movement associated with freezing of gait, such as when the patient is walking, turning, or stepping. The one or more processors determine, based on a difference between the first and second amplitudes, whether the patient suffers from or is susceptible to suffering from gait freezing. For example, if the one or more processors determine that the second amplitude of the bioelectrical signal sensed while patient 12 was performing the movement associated with freezing of gait is substantially less than the first amplitude of the bioelectrical signal sensed while patient 12 was not moving, the one or more processors determine that patient 12 suffers from or is susceptible to suffering from freezing of gait. In contrast, if the one or more processors determine that the second amplitude of the bioelectrical signal sensed while patient 12 was performing the movement associated with freezing of gait is approximately the same as the first amplitude of the bioelectrical signal sensed while patient 12 was not moving, the one or more processors determine that patient 12 does not suffer from freezing of gait. In some examples, the one or more processors output the determination of whether or not the patient suffers from or is susceptible to suffering from freezing of gait to a display on programmer 14.

Upon determining that the patient suffers from or is susceptible to suffering from freezing of gait, the one or more processors may program IMD 16 with therapy parameters defining electrical stimulation therapy configured to suppress freezing of gait. As described below, upon detecting that patient 12 is performing a movement associated with freezing of gait, IMD 16 delivers the electrical stimulation therapy configured to suppress freezing of gait so as to provide real-time therapy to suppress freezing of gait. In some examples, to suppress freezing of gait, the therapy is configured to mitigate or reduce a severity of an episode of freezing of gait in patient 12. In other examples, to suppress freezing of gait, the therapy is configured to terminate an occurring episode of freezing of gait experienced by patient 12. In other examples, to suppress freezing of gait, the therapy is configured to reduce or minimize the length of time that an episode of freezing of gait in patient 12 lasts. In other examples, to suppress freezing of gait, the therapy is configured to reduce the likelihood that patient 12 experiences an episode of freezing of gait. In other examples, to suppress freezing of gait, the therapy is configured to reduce the number of occurrences of an episode of freezing of gait in patient 12 over time.

As one example, patient 12 is determined to suffer from freezing of gait as described above. IMD 16 stores multiple DBS therapy settings in memory. For example, IMD 16 stores a first DBS therapy setting for providing therapy for symptoms of Parkinson's disease other than freezing of gait, such as bradykinesia, rigidity, or tremor. In one example, the first DBS therapy for providing therapy for symptoms of Parkinson's disease other than freezing of gait may further includes a first frequency selected from a range of approximately 130 Hertz to approximately 185 Hertz. Further, in some examples, the first DBS therapy for providing therapy for symptoms of Parkinson's disease other than freezing of gait may include a pulse width of approximately 10 microseconds to approximately 450 microseconds, such as, e.g., a pulse width of approximately 300 microseconds in other examples. In an example current-controlled system, the first DBS therapy for providing therapy for symptoms of Parkinson's disease other than freezing of gait may include a current amplitude of approximately 0.1 milliamps to approximately 25 milliamps, such as, e.g., approximately 10 milliamps. In an example voltage-controlled system, the first DBS therapy for providing therapy for symptoms of Parkinson's disease other than freezing of gait may include a voltage amplitude of approximately 0.1 Volts to approximately 25 Volts, such as, e.g., a voltage amplitude of approximately 10 Volts. Other values for the described therapy parameters are contemplated.

Further, IMD 16 stores a second DBS therapy setting for providing therapy for freezing of gait in patient 12. In one example, the second DBS therapy setting for providing therapy for freezing of gait includes a second frequency selected from a range of about 60 Hertz to about 100 Hertz, such as, e.g., a range of about 60 Hertz to about 70 Hertz. Further, the second DBS therapy setting for providing therapy for freezing of gait may further include a pulse width of approximately 10 microseconds to approximately 450 microseconds in some examples, such as, e.g., a pulse width of approximately 300 microseconds. In an example current-controlled system, the second DBS therapy setting for providing therapy for freezing of gait may further include a current amplitude of approximately 0.1 milliamps to approximately 25 milliamps in some examples, such as, e.g., a current amplitude of approximately 10 milliamps. In an example voltage-controlled system, the second DBS therapy setting for providing therapy for freezing of gait may further include a voltage amplitude of approximately 0.1 Volts to approximately 25 Volts, such as, e.g., a voltage amplitude of approximately 10 Volts.

During typical use, IMD 16 delivers DBS therapy at the first frequency to provide therapy for symptoms of Parkinson's disease in patient 12 other than freezing of gait, such as bradykinesia, rigidity, or tremor. Further, IMD 16 monitors patient 12 for movement via one or more sensors. In some examples, the one or more sensors include external sensors 31, which may include as accelerometers, pressure sensors, or magnetometers. In other examples, the one or more sensors include implantable sensors such as electrodes 24, 26. Upon detecting a movement of the patient associated with freezing of gait, such as transitioning from standing into stepping, walking, or turning, the IMD switches from delivering the DBS therapy at the first frequency configured to provide therapy for other symptoms of Parkinson's disease to delivering the DBS therapy at the second frequency configured to provide therapy for freezing of gait.

Further, upon detecting that the patient has ceased the movement associated with freezing of gait, IMD 16 switches from delivering the DBS therapy at the second frequency configured to provide therapy for freezing of gait to delivering the DBS therapy at the first frequency configured to provide therapy for the other undesirable symptoms of Parkinson's disease.

In this fashion, during normal operation, IMD 16 may provide therapy to patient 12 to suppress symptoms of Parkinson's disease in patient 12 other than freezing of gait, such as bradykinesia, rigidity, or tremor. Further, IMD 16 may detect that patient 12 is transitioning to a movement associated with freezing of gait, and so switch, in real time, to providing therapy to suppress freezing of gait. Upon detecting that patient 12 is no longer performing the movement associated with freezing of gait, IMD 16 may return to providing therapy to patient 12 to suppress the other symptoms. Accordingly, IMD 16 may be more flexible in the delivery of therapy provided to patient 12 than other systems that are not able to detect freezing of gait.

Figure 2:
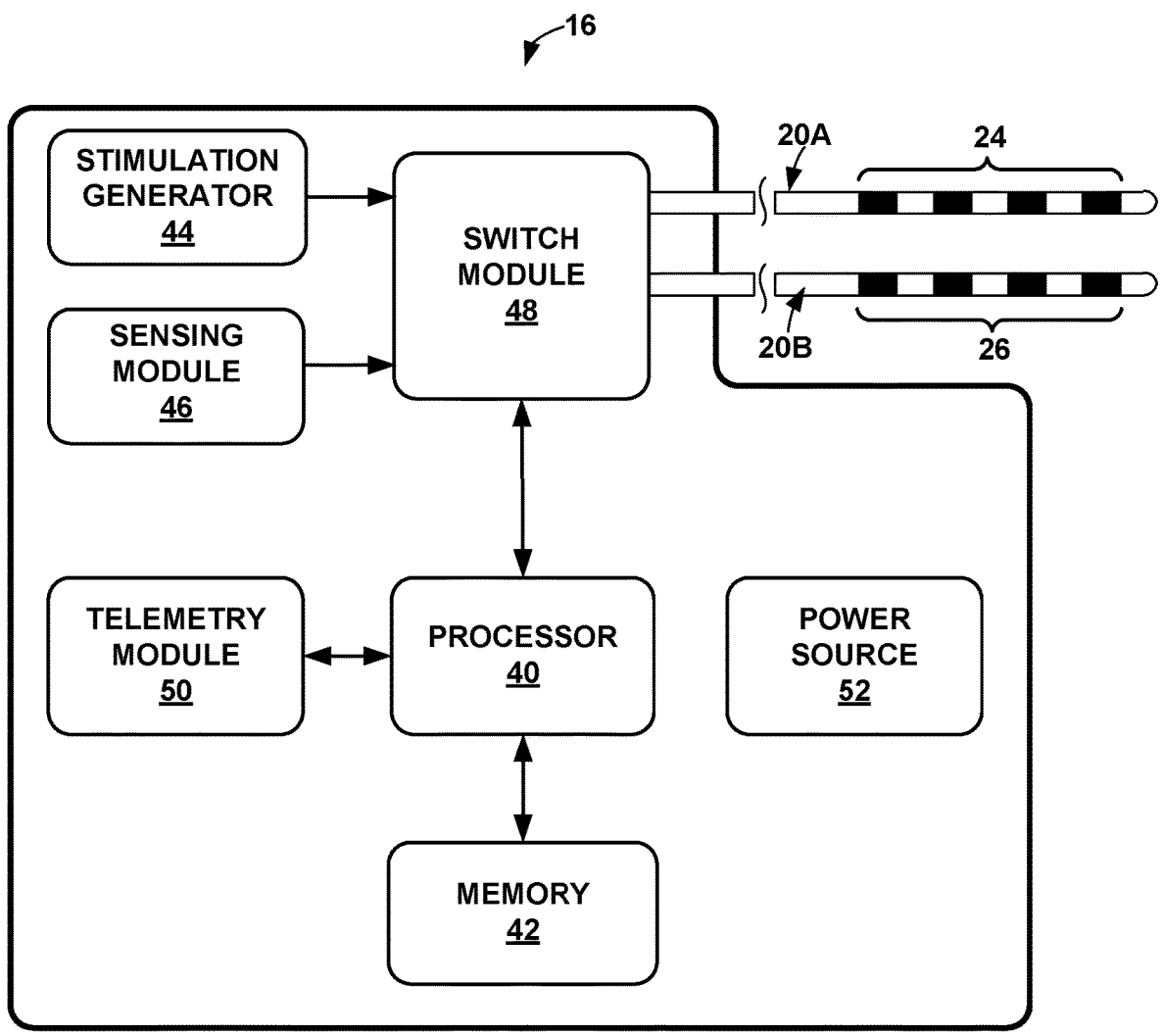
FIG. 2 is functional block diagram illustrating components of an example medical device for delivering electrical stimulation therapy in accordance with the techniques of the disclosure.

FIG. 2 is a functional block diagram illustrating components of an example IMD 16. In the example shown in FIG. 2, IMD 16 includes memory 40, processor 42, stimulation generator 44, sensing module 46, switch module 48, telemetry module 50, and power source 52. Processor 42 may include any one or more microprocessors, controllers, digital signal processors (DSPs), application specific integrated circuits (ASICs), field-programmable gate arrays (FPGAs), and discrete logic circuitry. The functions attributed to processors described herein, including processor 42, may be provided by a hardware device and embodied as software, firmware, hardware, or any combination thereof.

In the example shown in FIG. 2, sensing module 46 senses physiological signals of brain 28 of patient 12 via select combinations of electrodes 24, 26. Sensing module 46 may include circuitry that measures the electrical activity of a particular region, e.g., an anterior nucleus, thalamus or cortex of brain 24 via select electrodes 24, 26. For treatment of Parkinson's disease, sensing module 46 may be configured to measure the electrical activity of the subthalamic nucleus (STN), globus pallidus interna (GPi), globus pallidus externa (GPe), and/or other areas of the basal ganglia.

Sensing module 46 may sample the bioelectrical brain signal substantially continuously or at regular intervals, such as, but not limited to, a frequency of about 1 Hz to about 1000 Hz, such as about 250 Hz to about 1000 Hz or about 500 Hz to about 1000 Hz. Sensing module 46 includes circuitry for determining a voltage difference between two electrodes 24, 26, which generally indicates the electrical activity within the particular region of brain 24. One of the electrodes 26, 24 may act as a reference electrode, and, if sensing module 46 is implanted within patient 12, a housing of IMD 16 or the sensing module in examples in which sensing module 46 is separate from IMD 16, may include one or more electrodes that may be used to sense bioelectrical brain signals.

The output of sensing module 46 may be received by processor 42. In some cases, processor 42 may apply additional processing to the bioelectrical signals, e.g., convert the output to digital values for processing and/or amplify the bioelectrical brain signal. In addition, in some examples, sensing module 46 or processor 42 may filter the signal from the selected electrodes 24, 26 in order to remove undesirable artifacts from the signal, such as noise from cardiac signals generated within the body of patient 12. Although sensing module 46 is incorporated into a common outer housing with stimulation generator 44 and processor 42 in FIG. 2, in other examples, sensing module 46 is in a separate outer housing from the outer housing of IMD 16 and communicates with processor 42 via wired or wireless communication techniques. In other examples, a bioelectrical brain signal may be sensed via external electrodes (e.g., scalp electrodes).

In some examples, sensing module 46 may include circuitry to tune to and extract a power level of a particular frequency band of a sensed brain signal. Thus, the power level of a particular frequency band of a sensed brain signal may be extracted prior to digitization of the signal by processor 34. By tuning to and extracting the power level of a particular frequency band before the signal is digitized, it may be possible to run frequency domain analysis algorithms at a relatively slower rate compared to systems that do not include a circuit to extract a power level of a particular frequency band of a sensed brain signal prior to digitization of the signal. In some examples, sensing module 46 may include more than one channel to monitor simultaneous activity in different frequency bands, i.e., to extract the power level of more than one frequency band of a sensed brain signal. These frequency bands may include an alpha frequency band (e.g., 8 Hz to 12 Hz, beta frequency band (e.g., about 12 Hertz to about 35 Hertz), gamma frequency band (e.g., between about 35 Hertz to about 200 Hertz), or other frequency bands.

In some examples, sensing module 26 may include an architecture that merges chopper-stabilization with heterodyne signal processing to support a low-noise amplifier. In some examples, sensing module 26 may include a frequency selective signal monitor that includes a chopper-stabilized superheterodyne instrumentation amplifier and a signal analysis unit. Example amplifiers that may be included in the frequency selective signal monitor are described in further detail in commonly-assigned U.S. Patent Publication No. 2009/0082691 to Denison et al., entitled, "FREQUENCY SELECTIVE MONITORING OF PHYSIOLOGICAL SIGNALS" and filed on Sep. 25, 2008. U.S. Patent Publication No. 2009/0082691 to Denison et al. is incorporated herein by reference in its entirety.

As described in U.S. Patent Publication No. 2009/0082691 to Denison et al., a frequency selective signal monitor may utilize a heterodyning, chopper-stabilized amplifier architecture to convert a selected frequency band of a bioelectrical brain signal to a baseband for analysis. The bioelectrical brain signal may be analyzed in one or more selected frequency bands to detect amplitudes of bioelectrical brain signals within a particular frequency band, such as a Beta frequency, and, in response, deliver electrical stimulation therapy in accordance with some of the techniques described herein. The frequency selective signal monitor may provide a physiological signal monitoring device comprising a physiological sensing element that receives a physiological signal, an instrumentation amplifier comprising a modulator that modulates the signal at a first frequency, an amplifier that amplifies the modulated signal, and a demodulator that demodulates the amplified signal at a second frequency different from the first frequency. A signal analysis unit may analyze a characteristic of the signal in the selected frequency band. The second frequency may be selected such that the demodulator substantially centers a selected frequency band of the signal at a baseband.

In some examples, sensing module 46 may sense brain signals substantially at the same time that IMD 16 delivers therapy to patient 14. In other examples, sensing module 46 may sense brain signals and IMD 16 may deliver therapy at different times.

In some examples, sensing module 46 may monitor one or more physiological parameters of a patient other than that of bioelectrical brain signals, which are indicative of a movement associated with freeze of gait, in combination with the monitored physiological signal of the brain 28 of patient 12. Suitable patient physiological parameters may include, but are not limited to, muscle tone (e.g., as sensed via electromyography (EMG)), eye movement (e.g., as sensed via electroculography (EOG) or EEG), and body temperature. In some examples, patient movement may be monitored via actigraphy. In one example, processor 40 may monitor an EMG signal reflective of the muscle tone of patient 12 to identify physical movement of the patient associated with freeze of gait. Alternatively or additionally, processor 40 may monitor the physical movement of a patient associated with freeze of gait via one or more motion sensors, such as, e.g., one or more single or multi-axis accelerometer devices.

Memory 40 may include any volatile or non-volatile media, such as a random access memory (RAM), read only memory (ROM), non-volatile RAM (NVRAM), electrically erasable programmable ROM (EEPROM), flash memory, and the like. Memory 40 may store computer-readable instructions that, when executed by processor 42, cause IMD 16 to perform various functions described herein. Memory 40 may be considered, in some examples, a non-transitory computer-readable storage medium comprising instructions that cause one or more processors, such as, e.g., processor 42, to implement one or more of the example techniques described in this disclosure. The term "non-transitory" may indicate that the storage medium is not embodied in a carrier wave or a propagated signal. However, the term "non-transitory" should not be interpreted to mean that memory 40 is non-movable. As one example, memory 40 may be removed from IMD 16, and moved to another device. In certain examples, a non-transitory storage medium may store data that can, over time, change (e.g., in RAM).

In the example shown in FIG. 2, the set of electrodes 24 of lead 20A includes four electrodes, and the set of electrodes 26 of lead 20B includes four electrodes. Processor 42 controls switch module 48 to sense bioelectrical brain signals with selected combinations of electrodes 24, 26. In particular, switch module 48 may create or cut off electrical connections between sensing module 46 and selected electrodes 24, 26 in order to selectively sense bioelectrical brain signals, e.g., in particular portions of brain 28 of patient 12. Processor 42 may also control switch module 48 to apply stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 22A, 22B and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48. In some examples, IMD 16 may include separate current sources and sinks for each individual electrode (e.g., instead of a single stimulation generator) such that switch module 48 may not be necessary.

Stimulation generator 44 may be a single channel or multi-channel stimulation generator. For example, stimulation generator 44 may be capable of delivering, a single stimulation pulse or cycle, multiple stimulation pulses or a continuous signal at a given time via a single electrode combination or multiple stimulation pulses or sinusoidal waveforms at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

In one example memory 42 may store multiple electrical stimulation therapy parameter sets that define, for stimulation generator 44, electrical stimulation therapy for delivery to patient 12. For example, processor 40, based on a first electrical stimulation therapy parameter set stored in memory 42, may control stimulation generator 44 to deliver, to patient 12, a first electrical stimulation therapy configured to provide therapy for symptoms of Parkinson's disease other than freezing of gait, such as bradykinesia, rigidity, or tremor. In some examples, the first electrical stimulation therapy have a frequency selected from a range of about 130 Hertz to about 185 Hertz. As a further example, processor 40, based on a second electrical stimulation therapy parameter set stored in memory 42, may control stimulation generator 44 to deliver, to patient 12, a second electrical stimulation therapy configured to provide therapy for freeze of gait. In some examples, the second electrical stimulation therapy have a frequency selected from a range of about 60 Hertz to about 100 Hertz, such as, e.g., about 60 Hertz to about 70 Hertz.

Telemetry module 50 may support wireless communication between IMD 16 and an external programmer 14 or another computing device under the control of processor 42. Processor 42 of IMD 16 may, for example, transmit bioelectrical brain signals, seizure probability metrics for particular sleep stages, a seizure probability profile for patient 12, and the like via telemetry module 50 to a telemetry module within programmer 14 or another external device. Telemetry module 50 in IMD 16, as well as telemetry modules in other devices and systems described herein, such as programmer 14, may accomplish communication by radiofrequency (RF) communication techniques. In addition, telemetry module 50 may communicate with external programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

According to the techniques of the disclosure, processor 40 monitors, via sensing module 46 and one or more electrodes 24, 26 disposed along leads 20A-20B, a bioelectrical signal, such as a Beta signal, of brain 28 of patient 12. Processor 40 senses, via sensing module 46 and the one or more electrodes 24, 26, a first amplitude of the bioelectrical signal while patient 12 is not moving. Further, the one or more processors sense, via sensing module 46 and the one or more electrodes 24, 26, a second amplitude of the bioelectrical signal while patient 12 is performing a movement associated with freezing of gait, such as when the patient is walking, turning, or stepping. Processor 40 determines, based on a difference between the first and second amplitudes, whether patient 12 suffers from or is susceptible to suffering from gait freezing. For example, if processor 40 determines that the second amplitude of the bioelectrical signal sensed while patient 12 was performing the movement associated with freezing of gait is substantially less than the first amplitude of the bioelectrical signal sensed while patient 12 was not moving, processor 40 determines that patient 12 suffers from or is susceptible to suffering from freezing of gait. In contrast, if processor 40 determines that the second amplitude of the bioelectrical signal sensed while patient 12 was performing the movement associated with freezing of gait is approximately the same as the first amplitude of the bioelectrical signal sensed while patient 12 was not moving, processor 40 determines that patient 12 does not suffer from freezing of gait. In some examples, processor 40 transmits, via telemetry module 50, the determination of whether or not patient 12 suffers from or is susceptible to suffering from freezing of gait to a display on programmer 14.

Upon determining that patient 12 suffers from or is susceptible to suffering from freezing of gait, processor 40 stores in memory 42 therapy parameters defining electrical stimulation therapy configured to suppress freezing of gait. As described below, upon detecting that patient 12 is performing a movement associated with freezing of gait, processor 40 controls stimulation generator 44 to deliver the electrical stimulation therapy configured to suppress freezing of gait so as to provide real-time therapy to suppress freezing of gait.

As one example, patient 12 is determined to suffer from freezing of gait as described above. Processor 40 stores multiple DBS therapy settings in memory 42. For example, processor 40 stores, in memory 42, a first DBS therapy setting including a first frequency for providing therapy for symptoms of Parkinson's disease in patient 12 other than freezing of gait, such as bradykinesia, rigidity, or tremor. In one example, the first frequency is selected from a range of about 130 Hertz to about 185 Hertz. Further, processor 40 stores, in memory 42, a second DBS therapy setting including a second frequency for providing therapy for freezing of gait in patient 12. In one example, the second frequency is selected from a range of about 60 Hertz to about 100 Hertz, such as, e.g., a range of about 60 Hertz to about 70 Hertz.

During typical use, processor 40 controls stimulation generator 44 to deliver DBS therapy at the first frequency to provide therapy for symptoms of Parkinson's disease in patient 12 other than freezing of gait, such as bradykinesia, rigidity, or tremor. Further, processor 40 monitors patient 12 for movement via sensors 31. Upon detecting a movement of patient 12 associated with freezing of gait, such as transitioning from standing into stepping, walking, or turning, processor 40 controls stimulation generator 44 to switch from delivering the DBS therapy at the first frequency configured to provide therapy symptoms of Parkinson's disease other than freezing of gait to delivering the DBS therapy at the second frequency configured to provide therapy for freezing of gait.

Further, upon detecting that patient 12 has ceased the movement associated with freezing of gait, processor 40 controls stimulation generator 44 to switch from delivering the DBS therapy at the second frequency configured to provide therapy for freezing of gait to delivering the DBS therapy at the first frequency configured to provide therapy for symptoms of Parkinson's disease other than freezing of gait.

Figure 3:
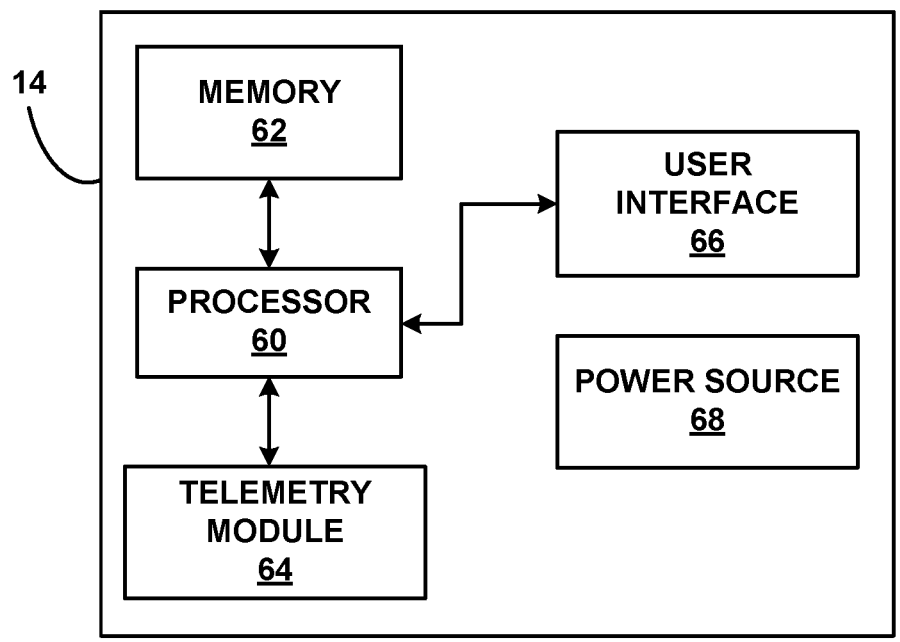
FIG. 3 is a functional block diagram illustrating components of an example medical device programmer.

FIG. 3 is a conceptual block diagram of an example external medical device programmer 14, which includes processor 60, memory 62, telemetry module 64, user interface 66, and power source 68. Processor 60 controls user interface 66 and telemetry module 64, and stores and retrieves information and instructions to and from memory 62. Programmer 14 may be configured for use as a clinician programmer or a patient programmer. Processor 60 may comprise any combination of one or more processors including one or more microprocessors, DSPs, ASICs, FPGAs, or other equivalent integrated or discrete logic circuitry. Accordingly, processor 60 may include any suitable structure, whether in hardware, software, firmware, or any combination thereof, to perform the functions ascribed herein to processor 60.

A user, such as a clinician or patient 12, may interact with programmer 14 through user interface 66. User interface 66 includes a display (not shown), such as a LCD or LED display or other type of screen, to present information related to treatment of the seizure disorder of patient 12. User interface 66 may also include an input mechanism to receive input from the user. The input mechanisms may include, for example, buttons, a keypad (e.g., an alphanumeric keypad), a peripheral pointing device or another input mechanism that allows the user to navigate though user interfaces presented by processor 60 of programmer 14 and provide input.

Memory 62 may include instructions for operating user interface 66 and telemetry module 64, and for managing power source 68. Memory 62 may also store any therapy data retrieved from IMD 16 during the course of therapy, as well as sensed bioelectrical brain signals. The clinician may use this therapy data to determine the progression of the patient condition in order to plan future treatment. Memory 62 may include any volatile or nonvolatile memory, such as RAM, ROM, EEPROM or flash memory. Memory 62 may also include a removable memory portion that may be used to provide memory updates or increases in memory capacities. A removable memory may also allow sensitive patient data to be removed before programmer 14 is used by a different patient.

Memory 62 may be considered, in some examples, a non-transitory computer-readable storage medium comprising instructions that cause one or more processors, such as, e.g., processor 60, to implement one or more of the example techniques described in this disclosure. The term "non-transitory" may indicate that the storage medium is not embodied in a carrier wave or a propagated signal. However, the term "non-transitory" should not be interpreted to mean that memory 62 is non-movable. As one example, memory 62 may be removed from programmer 14, and moved to another device. In certain examples, a non-transitory storage medium may store data that can, over time, change (e.g., in RAM).

Wireless telemetry in programmer 14 may be accomplished by RF communication or proximal inductive interaction of external programmer 14 with IMD 16. This wireless communication is possible through the use of telemetry module 64. Accordingly, telemetry module 64 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 68 may deliver operating power to the components of programmer 14. Power source 68 may include a battery and a power generation circuit to produce the operating power. In some examples, the battery may be rechargeable to allow extended operation.

Figure 4:
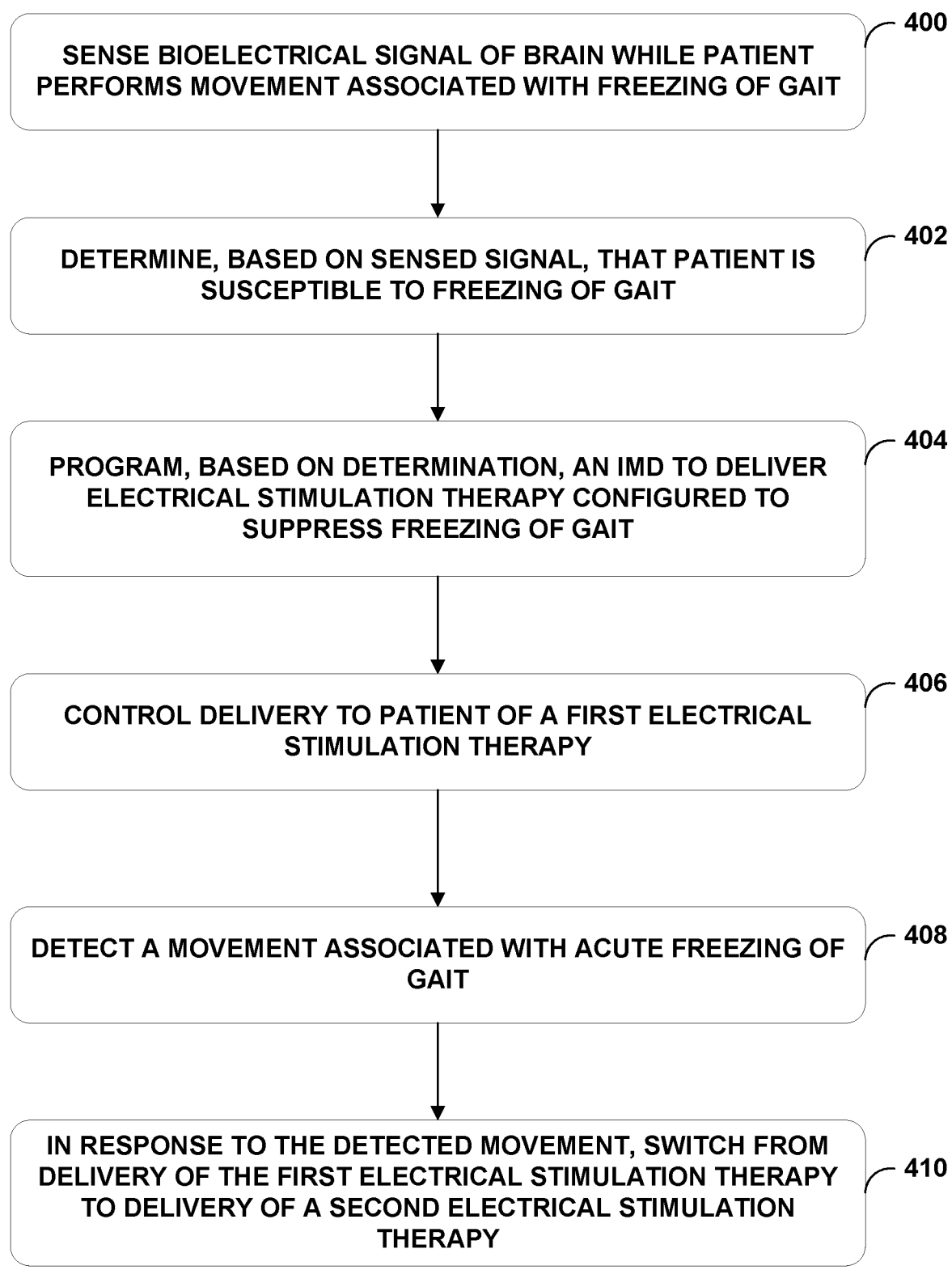
FIG. 4 is a flowchart illustrating an example technique for delivering electrical stimulation therapy to the brain of a patient in accordance with the techniques of the disclosure.

FIG. 4 is a flowchart illustrating an example technique for delivering electrical stimulation therapy to the brain of a patient in accordance with the techniques of the disclosure. For convenience, FIG. 4 is described with respect to FIG. 1. In the example of FIG. 4, one or more of processor 40 of IMD 16 and processor 60 of external programmer 14 determine whether patient 12 suffers from or is susceptible to suffering from gait freezing and programs IMD 16 to deliver therapy accordingly. In one example, the evaluation is performed by processor 40 of IMD 16. In another example, evaluation is performed by processor 60 of external programmer 14. In yet a further example, some or all of the functionality is apportioned between processor 40 of IMD 16 and processor 60 of external programmer 14.

In some examples, IMD 16 is implanted within patient 12 during a surgical procedure. Following the surgical procedure, a clinician may, using external programmer 14, program IMD 16 for delivery of therapy to patient 12 in an outpatient session. Further, during this outpatient session, the clinician may, in accordance with the techniques of the disclosure, determine whether patient 12 suffers from or is susceptible to suffering from freezing of gait. As one example, one or more of processors 40, 60 sense, via sensing module 46 and one or more electrodes 24, 26 disposed along leads 20A and 20B, a bioelectrical signal of brain 28 of patient 12 while patient 12 performs a movement associated with freezing of gait (400). In some examples, the one or more of processors 40, 60 sense a Beta signal comprising a frequency within about 11 Hertz to about 30 Hertz of brain 28 of patient 12. In some examples, the movement associated with freezing of gait is a turning movement, a stepping movement, or a transition from standing to stepping.

The one or more of processors 40, 60 determine, based on the sensed bioelectrical signal, that the patient is susceptible to freezing of gait (402). For example, one or more of processors 40, 60 sense, via sensing module 46 and the one or more electrodes 24, 26, a first amplitude of the bioelectrical signal while patient 12 is not moving. Further, the one or more of processors 40, 60 sense, via sensing module 46 and the one or more electrodes 24, 26, a second amplitude of the bioelectrical signal while patient 12 is performing the movement associated with freezing of gait. The one or more of processors 40, 60 determine, based on a difference between the first and second amplitudes, whether the patient suffers from or is susceptible to suffering from gait freezing. For example, if the one or more of processors 40, 60 determine that the second amplitude of the bioelectrical signal sensed while patient 12 was performing the movement associated with freezing of gait is less than a programmable threshold from the first amplitude of the bioelectrical signal sensed while patient 12 was not moving, the one or more of processors 40, 60 determine that patient 12 suffers from or is susceptible to suffering from freezing of gait. In some examples, a clinician determines the programmable threshold from a training phase in which patient 12 performs several moving and stationary tasks, and the neurological response of patient 12 is measured during the tasks. In this example, the clinician evaluates the neurological response of patient 12 to determine if patient 12 suffers from or is susceptible to suffering from freezing of gait. In contrast, if the one or more of processors 40, 60 determine that the second amplitude of the bioelectrical signal sensed while patient 12 was performing the movement associated with freezing of gait is approximately the same as the first amplitude of the bioelectrical signal sensed while patient 12 was not moving, the one or more of processors 40, 60 determine that patient 12 does not suffer from freezing of gait. In some examples, the one or more of processors 40, 60 output the determination of whether or not the patient suffers from or is susceptible to suffering from freezing of gait to a display on programmer 14.

Upon determining that patient 12 suffers from or is susceptible to suffering from freezing of gait, the one or more of processors 40, 60 outputs the determination to a display of user interface 66 of external programmer 14 for use by a clinician. In response, the clinician may program, via external programmer 14, IMD 16 to deliver electrical stimulation therapy configured to suppress freezing of gait in patient 12 (404). In one example, the clinician programs multiple DBS therapy settings in a memory of IMD 16. For example, the clinician may program, in IMD 16, a first DBS therapy setting including a first frequency for providing therapy for symptoms of Parkinson's disease other than freezing of gait, such as bradykinesia, rigidity, or tremor. In one example, the first frequency is selected from a range of about 130 Hertz to about 185 Hertz. Further, the clinician may program a second DBS therapy setting including a second frequency for providing therapy for freezing of gait in IMD 16. In one example, the second frequency is selected from a range of about 60 Hertz to about 100 Hertz, such as, e.g., a range of about 60 Hertz to about 70 Hertz.

During typical use, the one or more of processors 40, 60 control delivery, by IMD 16 and to patient 12, of a first electrical stimulation therapy at the first frequency (406). The one or more of processors 40, 60 detect a movement by patient 12 associated with freezing of gait (408). In some examples, processors 40, 60, detect the movement associated with freezing of gait via one or more sensors, such as one or more accelerometers, magnetometers, or pressure sensors. In other examples, processors 40, 60, detect the movement associated with freezing of gait by sensing one or more bioelectrical signals of the patient, such as via electrodes 24, 26 of leads 20A-20B. In yet other examples, processors 40, 60, detect the movement associated with freezing of gait by receiving an input from patient 12 via a patient programmer 14 indicating that patient 12 is or presently will be commencing the movement associated with freezing of gait. In some examples, the movement associated with freezing of gait is a stepping movement, a turning movement, or a transition from standing to stepping.

In response to the detected movement associated with freezing of gait, the one or more of processors 40, 60 control IMD 16 to switch from delivering the first electrical stimulation therapy to delivering the second electrical stimulation therapy (410). Thus, prior to the detected movement associated with freezing of gait, processors 40, 60 cause IMD 16 to deliver the first electrical stimulation therapy configured to suppress symptoms of Parkinson's disease other than freezing of gait, such as bradykinesia, rigidity, or tremor. However, such first electrical stimulation therapy may not be effective in suppressing freezing of gait in patient 12. Therefore, while detecting the movement associated with freezing of gait, processors 40, 60 cause IMD 16 to adjust the therapy such that the therapy is effective at suppressing episodes of freezing of gait in patient 12. The adjustment may include an adjustment of one or more stimulation parameters of the electrical stimulation therapy, such a frequency, a pulse-width, an amplitude, a combination of electrodes 24, 26, and/or a targeted region of tissue within brain 28 of patient 12.

In some examples, processors 40, 60 cause IMD 16 to resume delivering the first electrical stimulation therapy configured to suppress symptoms of Parkinson's disease other than freezing of gait. For example, upon detecting, via one or more sensors, that patient 12 is no longer performing the movement associated with freezing of gait, processors 40, 60 cause IMD 16 to resume delivering the first electrical stimulation therapy configured to suppress symptoms of Parkinson's disease other than freezing of gait. In yet further examples, in response to receiving an input from patient 12 via patient programmer 14, processors 40, 60 cause IMD 16 to resume delivering the first electrical stimulation therapy configured to suppress symptoms of Parkinson's disease other than freezing of gait. Accordingly, in this fashion, IMD 16 may provide real-time adjustments to the therapy so as to suppress freezing of gait when the patient commences activities or movements associated with freezing of gait. Further, IMD 16 may provide therapy effective at suppressing other symptoms of Parkinson's disease when patient 12 is not performing activities or movements associated with freezing of gait and therefore may not require specific therapy for suppressing freezing of gait.

Figure 5:
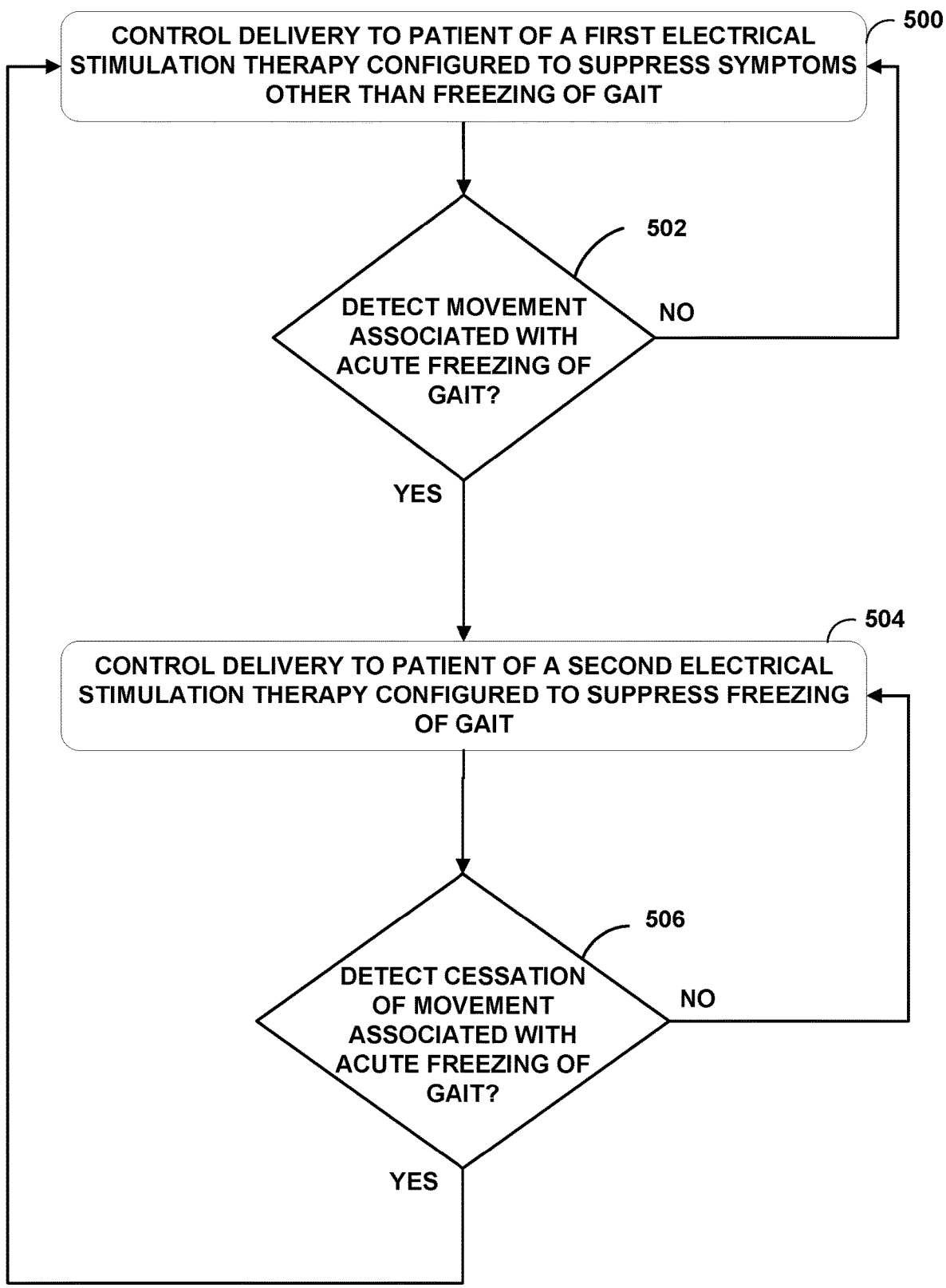
FIG. 5 is a flowchart illustrating an example technique for delivering electrical stimulation therapy to the brain of a patient in accordance with the techniques of the disclosure.

FIG. 5 is a flowchart illustrating an example technique for delivering electrical stimulation therapy to the brain of a patient in accordance with the techniques of the disclosure. For convenience, FIG. 5 is described with respect to FIG. 1.

As depicted by FIG. 5, processor 40 controls delivery, via stimulation generator 44 and electrodes 24, 26 disposed along leads 20A-20B, of a first electrical stimulation therapy to patient 12 (500). In one example, the first electrical stimulation is configured to suppress a symptom of a disease other than freezing of gait. For example, the first electrical stimulation may be configured to suppress symptoms of Parkinson's disease in patient 12 other than freezing of gait, such as bradykinesia, rigidity, or tremor. In some examples, the first electrical stimulation has a first frequency is selected from a range of about 130 Hertz to about 185 Hertz.

While delivering the first electrical stimulation, processor 40 detects, via one or more sensors, whether patient 12 is performing a movement associated with freezing of gait (502). In one example, the one or more sensors include one or more accelerometers. If processor 40 does not detect that patient 12 is performing a movement associated with freezing of gait ("NO" block of 502), then processor 40 continues to control delivery of the first electrical stimulation to patient 12 (500).

If processor 40 detects that patient 12 is performing a movement associated with freezing of gait ("YES" block of 502), then processor 40 controls delivery, via stimulation generator 44 and electrodes 24, 26 disposed along leads 20A-20B, of a second electrical stimulation therapy to patient 12 (504). In one example, the second electrical stimulation therapy is configured to suppress freezing of gait. In some examples, the second electrical stimulation therapy has a second frequency is selected from a range of about 60 Hertz to about 100 Hertz, such as, e.g., a range of about 60 Hertz to about 70 Hertz.

While delivering the second electrical stimulation therapy, processor 40 detects, via the one or more sensors, whether patient 12 has ceased the movement associated with freezing of gait (506). If processor 40 detects that patient 12 continues the movement associated with freezing of gait ("NO" block of 506), then processor 40 continues to control delivery of the second electrical stimulation therapy to patient 12 (504). If processor 40 detects that patient 12 has ceased the movement associated with freezing of gait ("YES" block of 506), then processor 40 controls delivery of the first electrical stimulation therapy to patient 12 (500).

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
 sensing, by one or more processors and via one or more electrodes, a bioelectrical signal of a brain of a patient while the patient performs movement associated with freezing of gait and while the patient is not experiencing an episode of freezing of gait;
 determining, by the one or more processors and based on the bioelectrical signal, that the patient is susceptible to freezing of gait while the patient is not experiencing an episode of freezing of gait; and
 in response to determining that the patient is susceptible to freezing of gait, programming, by the one or more processors, a medical device to:
  detect movement associated with freezing of gait; and
  deliver, to the patient and in response to detecting the movement associated with freezing of gait, electrical stimulation therapy configured to suppress freezing of gait.

2. The method of claim 1, wherein sensing the bioelectrical signal of the brain of the patient while the patient performs movement associated with freezing of gait comprises:
 sensing, while the patient is not moving, the bioelectrical signal; and
 sensing, while the patient performs movement associated with freezing of gait, the bioelectrical signal.

3. The method of claim 2, wherein determining, based on the bioelectrical signal, that the patient is susceptible to freezing of gait comprises:
 determining that an amplitude of the bioelectrical signal sensed while the patient is moving is substantially less than an amplitude of the bioelectrical signal sensed while the patient is not moving; and based on the determination that the amplitude of the bioelectrical signal sensed while the patient is moving is substantially less than the amplitude of the bioelectrical signal sensed while the patient is not moving, determining that the patient is susceptible to freezing of gait.

4. The method of claim 2, wherein movement associated with freezing of gait comprises at least one of a turning movement, a stepping movement, or a transition from a standing movement to a stepping movement.

5. The method of claim 1, wherein the bioelectrical signal of the brain of the patient is a Beta signal of the brain of the patient comprising a frequency from about 11 Hertz to about 30 Hertz.

6. The method of claim 1, wherein sensing the bioelectrical signal of the brain of the patient comprises sensing local field potentials (LFPs) of the brain of the patient.

7. The method of claim 1, wherein the bioelectrical signal is a biomarker associated with freezing of gait in the patient.

8. The method of claim 1, further comprising:
after programming the medical device to detect the movement associated with freezing of gait and deliver the electrical stimulation therapy configured to suppress freezing of gait:
controlling, by the one or more processors, the medical device to deliver a first electrical stimulation therapy at a first frequency to the patient;
detecting, by the one or more processors, the movement associated with freezing of gait; and
switching, by the one or more processors and in response to detecting the movement associated with freezing of gait, from controlling the medical device to deliver the first electrical stimulation therapy at the first frequency to the patient to controlling the medical device to deliver the electrical stimulation therapy configured to suppress freezing of gait to the patient, the electrical stimulation therapy configured to suppress freezing of gait comprising a second electrical stimulation therapy at a second frequency different from the first frequency.

9. The method of claim 8,
wherein the first frequency is selected from a range of about 130 Hertz to about 185 Hertz; and
wherein the second frequency is selected from a range of about 60 Hertz to about 100 Hertz.

10. The method of claim 8,
wherein the second electrical stimulation therapy is configured to suppress freezing of gait due to Parkinson's disease in the patient, and
wherein the first electrical stimulation therapy is configured to suppress one or more symptoms of Parkinson's disease in the patient other than freezing of gait.

11. The method of claim 8, further comprising:
detecting, by the one or more processors, cessation of the movement associated with freezing of gait; and
switching, by the one or more processors and in response to detecting the cessation of the movement associated with freezing of gait, from controlling the medical device to deliver the second electrical stimulation therapy at the second frequency to the patient to controlling the medical device to deliver the first electrical stimulation therapy at the first frequency to the patient.

12. A medical system comprising:
one or more electrodes; and
one or more processors configured to:
sense, via the one or more electrodes, a bioelectrical signal of a brain of a patient while the patient performs movement associated with freezing of gait and while the patient is not experiencing an episode of freezing of gait;
determine, based on the bioelectrical signal, that the patient is susceptible to freezing of gait while the patient is not experiencing an episode of freezing of gait; and
in response to determining that the patient is susceptible to freezing of gait, program a medical device to:
detect movement associated with freezing of gait; and
deliver, to the patient and in response to detecting the movement associated with freezing of gait, electrical stimulation therapy configured to suppress freezing of gait.

13. The medical system of claim 12, wherein, to sense the bioelectrical signal of the brain of the patient, the one or more processors are further configured to:
sense, via the one or more electrodes and while the patient is not moving, the bioelectrical signal; and
sense, via the one or more electrodes and while the patient performs movement associated with freezing of gait, the bioelectrical signal.

14. The medical system of claim 13, wherein, to determine, based on the bioelectrical signal, that the patient is susceptible to freezing of gait, the one or more processors are further configured to:
determine that an amplitude of the bioelectrical signal sensed while the patient is moving is substantially less than an amplitude of the bioelectrical signal sensed while the patient is not moving; and
based on the determination that the amplitude of the bioelectrical signal sensed while the patient is moving is substantially less than the amplitude of the bioelectrical signal sensed while the patient is not moving, determine that the patient is susceptible to freezing of gait.

15. The medical system of claim 13, wherein movement associated with freezing of gait comprises at least one of a turning movement, a stepping movement, or a transition from a standing movement to a stepping movement.

16. The medical system of claim 12, wherein the bioelectrical signal of the brain of the patient is a Beta signal of the brain of the patient comprising a frequency of about 11 Hertz to about 30 Hertz.

17. The medical system of claim 12, wherein, to sense the bioelectrical signal of the brain of the patient, the one or more processors are further configured to sense, via the one or more electrodes, local field potentials (LFPs) of the brain of the patient.

18. The medical system of claim 12, wherein the bioelectrical signal is a biomarker associated with freezing of gait in the patient.

19. The medical system of claim 12, wherein, after programming the medical device to detect the movement associated with freezing of gait and deliver the electrical stimulation therapy configured to suppress freezing of gait, the one or more processors are further configured to:

control delivery, by the medical device, of a first electrical stimulation therapy at a first frequency to the patient;

detect the movement associated with freezing of gait; and switch, in response to detecting the movement associated with freezing of gait, from controlling delivery, by the medical device, of the first electrical stimulation therapy at the first frequency to the patient to controlling delivery, by the medical device, of the electrical stimulation therapy configured to suppress freezing of gait to the patient, the electrical stimulation therapy configured to suppress freezing of gait comprising a second electrical stimulation therapy at a second frequency different from the first frequency.

20. The medical system of claim 19, wherein the first frequency is selected from a range of about 130 Hertz to about 185 Hertz; and wherein the second frequency is selected from a range of about 60 Hertz to about 70 Hertz.

21. The medical system of claim 19, wherein the second electrical stimulation therapy is configured to suppress freezing of gait due to Parkinson's disease in the patient, and wherein the first electrical stimulation therapy is configured to suppress one or more symptoms of Parkinson's disease in the patient other than freezing of gait.

22. The medical system of claim 19, wherein the one or more processors are further configured to:

detect cessation of the movement associated with freezing of gait; and switch, in response to detecting the cessation of the movement associated with freezing of gait, from delivering the second electrical stimulation therapy at the second frequency to the patient to delivering the first electrical stimulation therapy at the first frequency to the patient.

23. A non-transitory computer-readable medium comprising instructions, that, when executed, cause one or more processors to:

sense, via one or more electrodes, a bioelectrical signal of a brain of a patient while the patient performs movement associated with freezing of gait and while the patient is not experiencing an episode of freezing of gait;

determine, based on the bioelectrical signal, that the patient is susceptible to freezing of gait while the patient is not experiencing an episode of freezing of gait; and in response to determining that the patient is susceptible to freezing of gait, program a medical device to:

detect movement associated with freezing of gait; and deliver, to the patient and in response to detecting the movement associated with freezing of gait, electrical stimulation therapy configured to suppress freezing of gait.

24. The computer-readable medium of claim 23, wherein the instructions further cause the one or more processors to:

after programming the medical device to detect the movement associated with freezing of gait and deliver the electrical stimulation therapy configured to suppress freezing of gait:

control the medical device to deliver a first electrical stimulation therapy at a first frequency to the patient;

detect the movement associated with freezing of gait; and switch, in response to detecting the movement associated with freezing of gait, from controlling the medical device to deliver the first electrical stimulation therapy at the first frequency to the patient to controlling the medical device to deliver the electrical stimulation therapy configured to suppress freezing of gait to the patient, the electrical stimulation therapy configured to suppress freezing of gait comprising a second electrical stimulation therapy at a second frequency different from the first frequency.

25. A medical system comprising:

means for sensing a bioelectrical signal of a brain of a patient while the patient performs movement associated with freezing of gait and while the patient is not experiencing an episode of freezing of gait;

means for determining, based on the bioelectrical signal, that the patient is susceptible to freezing of gait while the patient is not experiencing an episode of freezing of gait; and means for programming, in response to determining that the patient is susceptible to freezing of gait, a medical device to:

detect movement associated with freezing of gait; and deliver, to the patient and in response to detecting the movement associated with freezing of gait, electrical stimulation therapy configured to suppress freezing of gait.

26. The medical system of claim 25, further comprising:

means for controlling the medical device to deliver a first electrical stimulation therapy at a first frequency to the patient after programming the medical device to detect the movement associated with freezing of gait and deliver the electrical stimulation therapy configured to suppress freezing of gait;

means for detecting the movement associated with freezing of gait; and means for switching, in response to detecting the movement associated with freezing of gait, from controlling the medical device to deliver the first electrical stimulation therapy at the first frequency to the patient to controlling the medical device to deliver the electrical stimulation therapy configured to suppress freezing of gait to the patient, the electrical stimulation therapy configured to suppress freezing of gait comprising a second electrical stimulation therapy at a second frequency different from the first frequency.

\* \* \* \* \*